(12) United States Patent
Peuker et al.

(10) Patent No.: US 10,143,535 B2
(45) Date of Patent: Dec. 4, 2018

(54) CONTAINER FOR STORING AND DISPENSING A LIQUID

(71) Applicant: 3M INNOVATIVE PROPERTIES COMPANY, St. Paul, MN (US)

(72) Inventors: Marc Peuker, Schoendorf (DE); Andreas J. Boehm, Reichling (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/327,763

(22) PCT Filed: Jul. 23, 2015

(86) PCT No.: PCT/US2015/041691
§ 371 (c)(1),
(2) Date: Jan. 20, 2017

(87) PCT Pub. No.: WO2016/014764
PCT Pub. Date: Jan. 28, 2016

(65) Prior Publication Data
US 2017/0209237 A1 Jul. 27, 2017

(30) Foreign Application Priority Data
Jul. 24, 2014 (EP) .................................... 14178273

(51) Int. Cl.
*A61C 5/64* (2017.01)
*B65D 81/32* (2006.01)
(Continued)

(52) U.S. Cl.
CPC .......... *A61C 5/64* (2017.02); *B05C 17/00553* (2013.01); *B05C 17/00576* (2013.01); *B65D 47/305* (2013.01); *B65D 81/3255* (2013.01)

(58) Field of Classification Search
CPC .. A61C 5/68; A61C 5/66; B05C 17/00; B05C 17/00553; B05C 17/00576; B65D 81/3255; B65D 47/305; A61B 17/00491
(Continued)

(56) References Cited

U.S. PATENT DOCUMENTS 4,941,751 A * 7/1990 Muhlbauer .............. A61C 5/64
206/217
5,037,592 A 8/1991 Erlenbach
(Continued)

FOREIGN PATENT DOCUMENTS

CN 102434095 5/2012
EP 1254750 11/2002
(Continued)

OTHER PUBLICATIONS

International Search Report for PCT International Application No. PCT/US2015/041691 dated Oct. 7, 2015, 3 pages.

*Primary Examiner* — Lien Ngo

(57) ABSTRACT

A container for storing and dispensing a liquid has a generally cup-shaped receptacle formed by a circumferential side wall and a front wall. A piston is slidably accommodated within the receptacle. The receptacle and the piston in combination form a chamber in which the liquid is received. The piston forms a sealing structure bearing on an inner surface of the side wall. The inner surface of the side wall has an arithmetic average surface roughness of between 0.05 μm and 4.5 μm R?a.#191 The container allows for air to penetrate in the chamber while it provides for the liquid to be captured therein.

12 Claims, 1 Drawing Sheet

(51) Int. Cl.
*B05C 17/005* (2006.01)
*B65D 47/30* (2006.01)

(58) Field of Classification Search
USPC .... 222/368, 135, 136, 145.5, 145.6; 433/89, 433/90; 206/219
See application file for complete search history.

(56) References Cited

U.S. PATENT DOCUMENTS

| | | | |
|---|---|---|---|
| 5,225,079 A | 7/1993 | Saito | |
| 5,392,904 A * | 2/1995 | Frick | A61C 5/64 206/219 |
| 9,220,578 B2 * | 12/2015 | Peuker | A61C 5/064 |
| 2003/0176834 A1 * | 9/2003 | Horth | B65D 81/3222 604/85 |
| 2004/0020796 A1 * | 2/2004 | Cheetham | A61C 5/64 206/63.5 |
| 2010/0261139 A1 | 10/2010 | Leiner | |
| 2011/0056853 A1 | 3/2011 | Cheetham | |
| 2011/0056984 A1 | 3/2011 | Cheetham | |
| 2012/0258422 A1 * | 10/2012 | Leiner | A61C 5/064 433/90 |
| 2015/0090745 A1 * | 4/2015 | Sasaki | A61C 5/064 222/536 |
| 2016/0045283 A1 * | 2/2016 | Boehm | A61C 5/064 433/90 |

FOREIGN PATENT DOCUMENTS

| | | |
|---|---|---|
| JP | 61-169146 | 7/1986 |
| JP | 2-102654 | 4/1990 |
| JP | 2002-191622 | 7/2002 |
| JP | 4106840 B2 * | 4/2008 |
| WO | 1998-46278 | 10/1998 |
| WO | WO 00/10479 A1 * | 3/2000 |
| WO | 2000-23002 | 4/2000 |
| WO | 2014-036236 | 3/2014 |
| WO | 2015-160552 | 10/2015 |

\* cited by examiner

CONTAINER FOR STORING AND DISPENSING A LIQUID

FIELD OF THE INVENTION

The invention relates to a container for storing and dispensing a liquid and in particular to a container having a receptacle and a piston. The piston has a sealing structure which bears on an inner surface of a side wall of the receptacle. The inner surface of the side wall has a rough surface and has an arithmetic average surface roughness of between 0.05 μm and 4.5 μm $R_a$.

BACKGROUND ART

Dental substances are often provided in devices allowing the substance to be dispensed directly to a desired location, for example on a dental pad or in a patient's mouth. Such dispensing devices typically have a chamber for holding the dental substance, an outlet, and a piston for extruding the substance from the chamber through the outlet.

A variety of dispensing devices are designed for dispensation of relatively high viscosity dental substances, like for example dental filling materials. Some of those dispensing devices are configured for use with an applicator providing an extrusion force that is sufficient for dispensation of high viscosity dental substances. In dentistry several types of manually operated applicators are available which provide leverage for increasing manual forces to provide sufficient extrusion forces. Many applicators are designed as a reusable tool which forms part of a dental practice's basic equipment.

A particular dispensing device often used to store, prepare and dispense a hardenable dental material mixed from a powder and a liquid is the so-called dental capsule in which the mixing of the powder and the liquid is performed within the capsule by shaking the capsule in a shaker.

US-A-2011/0056984 discloses container for mixing and dispensing material. The container comprises a body having a main chamber, a dispensing nozzle, a liquid receptacle and a plunger. The liquid receptacle has a front portion arranged to break away upon pressure being applied by the plunger so that the plunger can traverse the entire length of the body. This enables a charge of material in the main chamber to be entirely dispensed through a frangible wall into the nozzle. The container is particularly envisaged for use in mixing and dispensing of dental materials.

US-A-2010/261139 discloses a mixing and application capsule for producing and discharging a dental preparation. To prevent a liquid loss, a mixing and application capsule for producing a dental preparation is proposed. The capsule has a capsule body with a mixing chamber for receiving a mixing component and for mixing the dental preparation from the mixing component and a fluid. The capsule further has an outlet opening for discharging the dental preparation. A first plunger body which can be displaced in the capsule body delimits the mixing chamber in the capsule body. The first plunger body has a channel to guide the fluid from a cavity into the mixing chamber and a projection. The capsule has further a second plunger body which can be displaced in the capsule body relative to the first plunger body. The second plunger body has the cavity to receive the fluid. The cavity is configured to receive the projection of the first plunger body.

Such capsules have a variety of advantages as, for example, a relatively long shelf life. However there is still a desire for a capsule with such a long shelf life, which is easy to use and which is nevertheless relatively inexpensive.

SUMMARY OF THE INVENTION

The invention relates to a container for storing and dispensing a liquid, and to a capsule comprising such a container. The container and the capsule are preferably for dental use. The liquid container comprises a generally cup-shaped receptacle formed by a circumferential side wall and a front wall. The receptacle further has a rear opening formed by the side wall and a front opening extending through the front wall. The rear opening is closed by a piston which is slidably accommodated within the receptacle and the front opening is openably sealed. The receptacle and the piston in combination form a chamber in which the liquid is received. Further the piston forms a circumferential sealing structure which bears on an inner surface of the side wall. The inner surface of the side wall has an arithmetic average surface roughness of between 0.05 μm and 4.5 μm Ra.

The invention is advantageous in that it provides a container for storing a liquid in a tightly sealed configuration. Further the container allows storing of the liquid together with air but with keeping the air and the liquid in two separate bulks. Thus anaerobic polymerization of the liquid can be avoided without causing air bubbles in the liquid. Further a capsule as it may be used with the container of the invention is relatively easy to use and relatively inexpensive in manufacturing.

In one embodiment the circumferential side wall or the inner surface of the side wall extends along a longitudinal axis at a generally uniform cross-section, for example circular or elliptical. The front wall may extend radially, for example disc-shaped, to the longitudinal axis. Depending on the viscosity of the liquid the surface roughness may be adapted to adjust any air flow between the sealing structure and the inner surface of the side wall. For a higher viscous liquid the surface roughness may be higher than for a lower viscous liquid.

In a further embodiment the arithmetic average surface roughness of the inner surface of the side wall is essentially the same measured along the circumference and along a dimension perpendicular to the circumference. In particular the arithmetic average surface roughness of the inner surface of the side wall is essentially the same measured along the circumference and along a dimension of the longitudinal axis. Thus the effect of the surface roughness in essentially independent from the positioning of the piston relative to the receptacle.

In one embodiment the arithmetic average surface roughness of the sealing structure is lower than the arithmetic average surface roughness of the side wall. Thus forces for moving the piston into the container can be minimized. The arithmetic average surface roughness of the sealing structure may be about 0.01 μm and about 1.6 μm Ra.

In one embodiment the sealing structure and the inner surface of the side wall each have a generally circular cross-section. The diameter of the sealing structure is preferably greater than the diameter of the inner surface. Thus a press fit between the sealing structure and the inner surface is formed. The sealing structure may be a circumferential ridge or bulge, however, the skilled person will recognize that in one example the piston may be cylindrical and the outer cylindrical surface may also form the sealing structure. The diameter of the sealing structure may be about 100 μm greater than the diameter of the inner surface. Further the diameter of the piston may be between about 2 mm and about 30 mm.

In one embodiment the piston in made of at least one of polypropylene, high or low density polyethylene, or a thermoplastic elastomer, and wherein the receptacle is made of at least one of polyoxymethylene, polyamide, polybutadiene terephthalate, high density polyethylene, polypropylene, liquid crystal polymer, cyclic olefin polymer, or polyethylene terephthalate. In a preferred embodiment the piston and the receptacle each are made of a high density polyethylene. Preferably the piston and the receptacle are made by injection molding. The receptacle may also be made of two components, for example of a liquid crystal polymer forming an inner barrier layer against permeation of substances and a polyethylene forming a relatively mechanically stable outer layer.

In a further embodiment the inner side wall has a surface structure which corresponds to a negative surface structure of a sandblasted, an electrical discharge machined or an etched steel surface. For example the receptacle may be made by injection molding and the injection mold portion for shaping the inner surface may be finished by sandblasting, electrical discharge machining or etching. In contrast the piston may be made by injection molding and the injection mold portion for shaping the sealing structure may be finished by polishing. Accordingly the sealing structure may be more glossy or smoother than the inner surface of the side wall. The rough inner surface in combination with the smooth surface of the sealing structure thus preferably provides one or more open paths through an area in which inner surface and the sealing structure directly contact each other.

In a further embodiment the front opening is closed by a sealing foil which is attached at an outer surface of the front wall in a manner such that the foil overlaps the front opening and such that the foil and the front wall detach upon urging the foil and the front wall away from each other upon exceeding a predetermined threshold force. For example the liquid in the container may be pressurized by urging the piston into the receptacle and the pressurized liquid may exert a force greater than the threshold force to the foil so that the foil detaches (partly) from the front wall and opens the front opening. The container may be movably accommodated in a cartridge, for example of a capsule for dispensing a dental material. The container and the cartridge in combination may form a mixing chamber holding a powder material. The powder material and the liquid are preferably configured to form a dental material if mixed with each other. The cartridge may further have a nozzle which forms a valve with the cartridge. The nozzle may be movable between a storage position in which the valve closes an outlet of the second chamber and a dispensing position in which the valve opens the outlet of the mixing chamber.

In a further aspect of the invention a method is provided for making a container of the invention. The method may comprise the steps of:
  providing a mold having a mold portion for forming the inner side of the receptacle, the mold portion for forming the inner side of the receptacle having a surface being finished by sandblasting, electrical discharging or etching;
  providing a mold having a mold portion for forming the sealing structure, the mold portion for forming the sealing structure having a surface being finished by polishing; and
  injection molding the receptacle and the piston from at least one molten plastic material.

DETAILED DESCRIPTION OF THE INVENTION

Figure 1:
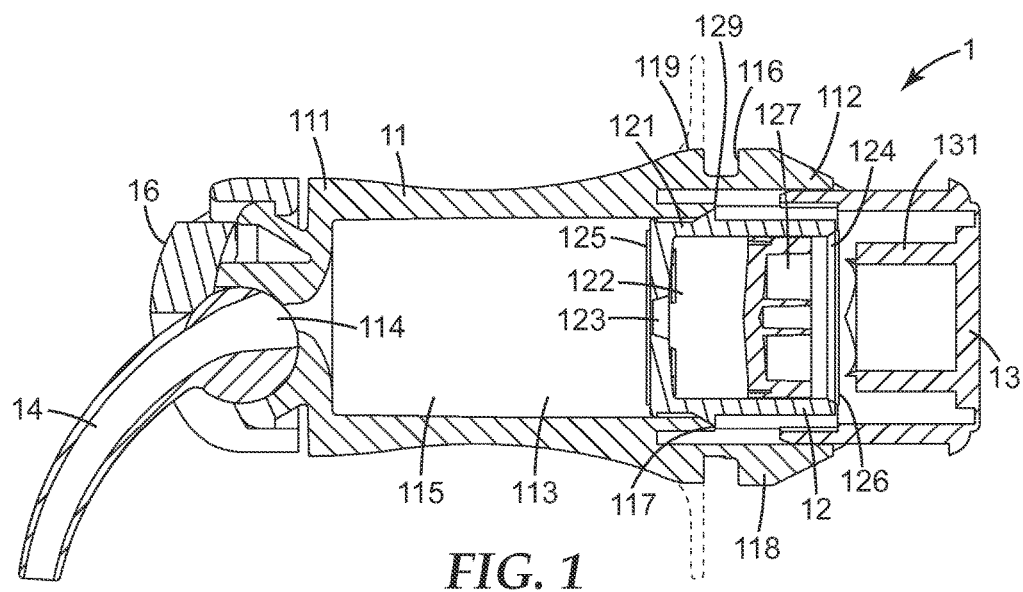
FIG. 1 is a cross-sectional view of a capsule according to an embodiment of the invention.

FIG. 1 shows a capsule 1 for mixing and dispensing a dental material. The capsule 1 has a capsule body 11 that has a front end 111 and a rear end 112. A cavity 113 extends from the rear end 112 into the capsule body 11. The cavity 113 merges adjacent the front end 111 of the capsule body 11 in an outlet 114 through the capsule body 11. The cavity 113 is closed by a liquid container 12. The liquid container 12 is positioned adjacent the rear end 112 of the capsule body 11 and spaced from the outlet 114. The space formed in the cavity 113 between the outlet 114, the capsule body 11 and the liquid container 12 forms a mixing chamber for mixing the dental material. At an initial stage as shown the mixing chamber is preferably (partially) filled with a powder material and the liquid container 12 is filled with a liquid. The capsule 1 is adapted to be activated by a user. Such an activation of the capsule 1 causes the liquid to be transferred into the mixing chamber.

The cavity 113 has a stepped configuration provided by a front section 115 and a wider rear section 116. Preferably the cavity 113 extends into the capsule body 11 at a generally circular cross-section. Further the front section 115 and the rear section 116 extend substantially concentrically and each at a generally uniform circular cross-section. Thus the transition between the front and rear section 115, 116 forms a step 117 in the cavity 113. The step 117 in forms a resistance for impeding a movement of the liquid container 12 within the front section 115 of the cavity 113. Therefore the liquid container 12 further has a detent 129, in the example a circumferential ridge or bulge, for cooperating with the resistance or step 117. In particular the detent 129 provides the liquid container 12 with a cross-section that is larger than the inner cross-section of the front section 115 of the cavity 113. Thus the cartridge 12 and the capsule body 11 are adapted such that the liquid container 12 can be only press fit within the front section 115 of the cavity 113.

The capsule 1 further has a plunger 13. The plunger 13 has a plug 131 which is receivable within the cartridge 12 through the rear opening 124, for pushing the piston 127 toward the front opening 123. The plug 131 has a cross-section that is sized and shaped substantially corresponding to the size and shape of the rear opening 124 of the receptacle 121. In the example the plug 131 and the rear opening 124 have a generally circular cross-section. Further the plug 131 may form a cutting edge (not shown in this view) for punching through the rear foil 126 of the liquid container 12.

Upon moving the plunger 13 into the liquid container 12 the liquid is transferred into the mixing chamber and gets in contact with the powder so that the capsule 1 is activated. At the activated stage the capsule 1 can be placed in an agitator (not shown) in which the capsule may be shaken to cause the powder and the liquid to mix with one another. The powder and the liquid are preferably adapted to form a hardenable composition in combination. An exemplary powder material comprises a glass powder or resin modified glass powder and an exemplary liquid comprises a water based polyacid or a monomer based polyacid with light initiator, and the mixture thereof comprises a glass-ionomer dental material. The mixture from the powder and the liquid typically forms a pasty material which can be dispensed through the outlet 114 of the capsule body by moving the plunger 13 and the liquid container 12 toward the outlet 114. For dispensing the dental material the capsule 1 further comprises a nozzle 14 which is attached adjacent the front end 111 of the capsule body 11. The nozzle 14 and the capsule body 11 are pivotable between a dispensing position (shown) and a storage position. In the dispensing position the nozzle 14 opens the outlet 114 of the capsule 1 for dispensing the dental material, whereas in the storage position the nozzle 14 closes the outlet 114. In the example the nozzle 14 is retained at the capsule body 11 by a cap 16. In another example the nozzle 14 and the capsule body 11 may however be molded into each other, for example by first molding the nozzle 14 and subsequently overmolding the nozzle 14 by the capsule body 11. Further the capsule 1 has a catch 118 for retaining the capsule 1 in a dispensing gun (not shown). Such a dispensing gun is for example commercially available under the designation 3M™ ESPE™ Capsule Dispenser form the company 3M Deutschland GmbH, Germany. The catch 118 in the example is formed by a circumferential bulge at the rear end 112 of the capsule body 11. A circumferential rim 119 is arranged spaced from the catch 118 further to the front end 111 of the capsule body.

As indicated by the dashed line the rim 119 may form a finger plate. The finger plate can assist in retaining the capsule manually while activating the capsule 1 for bringing the powder and the liquid in contact with each other.

Figure 2:
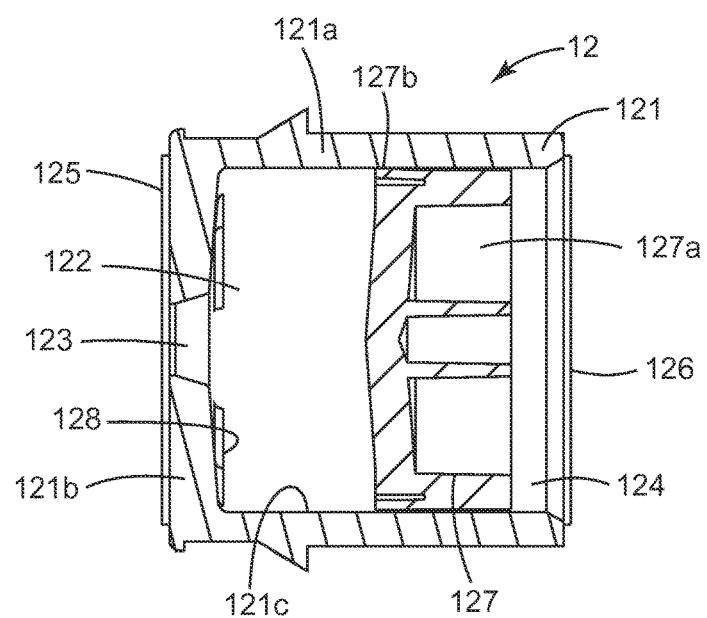
FIG. 2 shows a detail of FIG. 1.

FIG. 2 shows the liquid container 12 in more detail. The liquid container 12 comprises a receptacle 121. The receptacle 121 in the example is generally ring-shaped and forms a channel 122 therethrough. The channel 122 extends between a front opening 123 and a rear opening 124 of the receptacle 121. The receptacle 121 is preferably made of a plastic material, in particular may be made of a thermoplastic material, for example polyethyelene or polypropylene. The liquid container 12 further has a front foil 125 that closes the front opening 123 and an optional rear foil 126 that closes the rear opening 124. The front foil 125 and the optional rear foil 126 each comprise a contiguous layer of metal, preferably an aluminum layer. In one example the aluminum layer has a thickness of between 0.008 mm and 0.1 mm, preferably about 0.03 mm. The metal layer is preferably generally adapted to block substances, in particular air and moisture from permeating through the front and/or rear foil 125, 126. Preferably each of the front and the rear foil 125, 126 further comprise a polymeric layer, preferably a layer comprising or consisting of polyethylene. This allows for the front and the rear foil 125, 126 to be heat sealed with the polymeric layer to the thermoplastic receptacle 121. Heat sealing may be performed using a heated tool or by ultrasonic welding, for example. Further the thermoplastic layer forms a protective layer for the metal layer so as to avoid undesired chemical or physical interaction between the liquid and the metal layer.

The front foil 125 is attached at the receptacle 121 along a closed path circumferentially around the front opening 123, and the rear foil 126 is attached at the 121 along a closed path circumferentially around the rear opening 124. Thus the channel 122 is tightly sealed so that the front foil 125, the rear foil 126 and the receptacle 121 in combination form a closed liquid chamber. In the example the liquid chamber contains a liquid forming one component of the dental material, as described.

The front foil 125 and the receptacle 121 in at least a partial area of the circumferential path are separably sealed with each other. In the example the front foil 125 and the receptacle 121 are overall separably sealed with each other. Such a separable seal can be provided by heat sealing the front foil 125 with its polymeric layer oriented to the receptacle 121 for a predetermined time, at a predetermined temperature and a predetermined sealing pressure.

Thus the separably sealed area defines an openable valve through the circumferential path. In particular if the liquid is pressurized toward the sealed front opening 123 at a certain predetermined minimum or threshold pressure the interconnection between the front foil 125 and the receptacle 121 starts yielding and thus enables the liquid to creep between the front foil 125 and the receptacle 121. It has been found that the front foil 125 does not entirely separate from the receptacle 121. In contrast the liquid reproducibly creates only a passageway continuing from the front opening 123 toward an outer boundary of the front foil 125. Therefore the front foil 125 remains attached at the receptacle although a portion of the front foil 125 separates by liquid pressure.

To build up a pressure on the liquid a piston 127 is received in the channel 122 of the receptacle 121. The piston 127 is arranged between the front and rear opening 123, 124 of the receptacle 121. Therefore the piston 127 is sealed within the liquid chamber together with the liquid. In particular the piston 127 is received within the channel 122 and is movable along the channel 122. The piston 127 is arranged in the receptacle 121 such that the liquid is enclosed in the receptacle 12 between the front foil 125 and the piston 127. The piston 127 may be moved toward the front opening 123 for pressurizing the liquid toward the front opening, thus causing the valve to open and for transferring the liquid into the mixing chamber.

In the example the piston 127 is shaped to form a space 127a in which air is accommodated. With the piston 127 being sealed within the receptacle 121 the air is also hermetically sealed within the receptacle 121. The receptacle 121 is formed by a circumferential side wall 121a and a front wall 121b. The piston 127 forms a circumferential sealing structure 127b bearing on an inner surface 121c of the side wall 121a. The side wall 121a has an arithmetic average surface roughness of between 0.05 μm and 4.5 μm Ra, and in more particular an arithmetic average surface roughness of between 0.2 μm and 1.8 μm Ra. The surface roughness establishes a (minor) open path through areas in which the piston 127 and the receptacle 121 touch each other (at surface peaks). Accordingly although the piston 127 and the receptacle 121 in combination form a seal hindering the liquid to pass between the piston 127 and the receptacle 121, air can pass between the liquid chamber and the space 127a through the path established by the surface roughness. Any air sealed within the liquid chamber may be used to avoid anaerobic polymerization of the liquid. On the other hand the air and the liquid are separated by the piston so that any liquid transferred in the mixing chamber substantially does not contain air or air bubbles.

Therefore a reliable predetermined amount of liquid may be transferrable to the mixing chamber by movement of the piston 127 for a predetermined stroke. Further it has been found that in attempts to entirely empty the liquid chamber by moving the piston 127 in an end position adjacent the front opening 123 results in tolerances of the amount of liquid transferred. This is because as the piston 127 approaches the end position, the space between the piston 127 and the inside of the receptacle 12 gets smaller and the smaller the space the more is the liquid hindered in being displaced toward the front opening 123. Thus, depending on the viscosity of the liquid and any force at which the piston 127 is moved, a non foreseeable residual amount of liquid may be captured in that space. The receptacle 12 of the invention therefore has at least one stopper 128 which stops the piston 127 at a position prior to the end position. In other words the piston 127 and the receptacle 12 are shaped such that in the closest position of the piston 127 relative to the front opening 123 still sufficient space for easy displacement of the liquid is available between the piston 127 and the receptacle 12. Therefore the tolerances in the amount transferred to the mixing chamber can be minimized.

The invention claimed is:

1. A container for storing and dispensing a polymerizable liquid, comprising a generally cup-shaped receptacle formed by a circumferential side wall and a front wall and further having a rear opening formed by the side wall and a front opening extending through the front wall, the rear opening being closed by a piston which is slidably accommodated within the receptacle and the front opening being openably sealed, the receptacle and the piston in combination forming a chamber in which the polymerizable liquid is received, the piston forming a circumferential sealing structure bearing on an inner surface of the side wall, wherein the inner surface of the side wall has an arithmetic average surface roughness of between 0.05 µm and 4.5 µm $R_a$, and wherein the arithmetic average surface roughness of the sealing structure is lower than the arithmetic average surface roughness of the side wall to provide one or more open paths through an area in which the inner surface of the side wall and the circumferential sealing structure directly contact each other, and wherein the open paths are sufficiently air-permeable to prevent premature polymerization of the polymerizable liquid sealed within the chamber.

2. The container of claim 1, wherein the circumferential side wall or the inner surface of the side wall extends along a longitudinal axis at a generally uniform cross-section, and wherein the front wall extends radially to the longitudinal axis.

3. The container of claim 1, wherein the arithmetic average surface roughness of the inner surface of the side wall is essentially the same measured along the circumference and along a dimension perpendicular to the circumference.

4. The container of claim 1, wherein the arithmetic average surface roughness of the sealing structure is about 0.01 µm and about 1.6 µm $R_a$.

5. The container of claim 1, wherein the sealing structure and the inner surface of the side wall each have a generally circular cross-section, wherein the diameter of the sealing structure is greater than the diameter of the inner surface.

6. The container of claim 5, wherein the diameter of the sealing structure is about 100 µm greater than the diameter of the inner surface.

7. The container of claim 1, wherein the piston in made of polypropylene, high or low density polyethylene, or a thermoplastic elastomer, and wherein the receptacle is made of polyoxymethylene, polyamide, polybutadiene terephthalate, high density polyethylene, polypropylene, liquid crystal polymer, cyclic olefin polymer, or polyethylene terephthalate.

8. The container of claim 1, wherein the inner side wall has a surface structure which corresponds to a negative surface structure of a sandblasted steel surface.

9. The container of claim 8, wherein the sealing structure is smoother than the inner side wall.

10. The container of claim 1, wherein the front opening is closed by a sealing foil which is attached at an outer surface of the front wall in a manner such that the foil overlaps the front opening and such that the foil and the front wall detach upon urging the foil and the front wall away from each other upon exceeding a predetermined threshold force.

11. The container of claim 1, being movably accommodated in a cartridge, wherein the container and the cartridge in combination form a mixing chamber holding a powder material, and wherein the powder material and the liquid are configured to form a dental material if mixed with each other.

12. The container of claim 11, wherein the cartridge has a nozzle which forms a valve with the cartridge, wherein the nozzle is movable between a storage position in which the valve closes an outlet of the second chamber and a dispensing position in which the valve opens the outlet of the mixing chamber.

* * * * *